United States Patent

Elmore et al.

[11] Patent Number: 5,157,089
[45] Date of Patent: Oct. 20, 1992

[54] CITRIC ESTER DILUENTS

[75] Inventors: Jimmy D. Elmore, Louisville, Ky.; Elizabeth G. Zylla, Marengo, Ohio; George A. Roy, II, New Albany, Ind.

[73] Assignee: Hi-Tek Polymers, Inc., Jeffersontown, Ky.

[21] Appl. No.: 699,439

[22] Filed: May 13, 1991

Related U.S. Application Data

[60] Division of Ser. No. 588,705, Sep. 27, 1990, Pat. No. 5,089,658, which is a continuation-in-part of Ser. No. 248,732, Sep. 26, 1988, abandoned.

[51] Int. Cl.⁵ ............... C08F 2/00; C07C 69/66
[52] U.S. Cl. ............... 526/210; 560/182; 560/180
[58] Field of Search ............... 560/180; 526/210

[56] References Cited

U.S. PATENT DOCUMENTS 4,972,036 11/1990 Elmor ............... 526/210

Primary Examiner—Paul J. Killos
Attorney, Agent, or Firm—Herbert P. Price

[57] ABSTRACT

Citric ester compositions wherein the ester components contain about 1.5 to about 3 hydroxyl groups per molecule are useful as pigment grinding vehicles and as reactive diluents for thermosetting coatings.

13 Claims, No Drawings

CITRIC ESTER DILUENTS

CROSS REFERENCE TO RELATED APPLICATIONS

This is a division of copending application Ser. No. 07/588,705, filed Sep. 27, 1990, now U.S. Pat. No. 5,089,658, which is a continuation-in-part of application Ser. No. 07/248,732, filed Sep. 26, 1988, now abandoned.

BACKGROUND OF THE INVENTION

The field of art to which this invention pertains is citric esters.

Citric esters are well known compositions which have been used as plasticizers, lubricants and anti-settling additives for paints.

U.S. Pat. No. 2,122,716 describes long chain esters of citric acid, e.g., tridodecyl citrate, which have been used as plasticizers for resinous compositions.

U.S. Pat. No. 3,239,555 and 3,241,992 disclose bis-citric acid esters made by esterifying the acid groups with $C_1$ to $C_{18}$ alcohols and coupling the esters with dibasic acids. Such esters are useful as plasticizers for plastics.

In U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

Lubricants for tinplate are disclosed in U.S. Pat. No. 4,287,741. Such lubricants are citric esters wherein at least one acid group is esterified with a one to 10 carbon alcohol and the hydroxyl group can be esterified with a 1 to 10 carbon acid.

Polyesters made by reacting glycols and allyl alcohol with citric acid are described in U.S. Pat. No. 2,936,297.

In German Pat. No. 1,228,736, distearyl citrate is disclosed as being useful to prevent settling of pigments in paints.

Internal processing lubricants for thermoplastics made from copolyesters of aliphatic diols, citric acid and long-chain monohydric alcohols are disclosed in British Pat. No. 1,450,273.

SUMMARY OF INVENTION

This invention is directed to citric acid esters. In one aspect, this invention pertains to citric acid esters which contain at least one primary or secondary hydroxyl group. In another aspect, this invention relates to citric acid esters which are reactive diluents. In still another aspect, this invention pertains to citric esters which are pigment dispersants.

The citric ester composition of this invention has the formula:

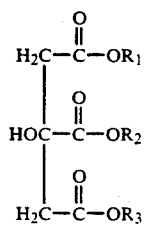

wherein $R_1$ and $R_2$ are selected from

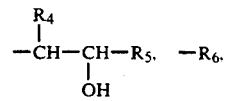

$-(CH_2)_xOH$, or mixtures thereof;

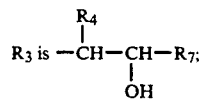

wherein $R_4$ and $R_5$ are H, or an alkyl, cycloalkyl, or an alkyl ester group containing 1 to about 32 carbon atoms wherein said alkyl ester group is derived from epoxidized esters of unsaturated acids or glycidyl esters of monocarboxylic acids, wherein the total number of carbon atoms in $R_4$ and $R_5$ are 0 to about 32; wherein $R_6$ is an alkyl group containing 1 to about 18 carbon atoms, or a cycloalkyl group containing 5 to about 10 carbon atoms; wherein $R_7$ is an alkyl, cycloalkyl or alkyl ester group containing 4 to about 32 carbon atoms wherein said alkyl ester group is derived from epoxidized esters of unsaturated acids or glycidyl esters of monocarboxylic acids; and wherein x has a value of 3 to 6. Each of these R groups is so selected that the total number of OH groups in $R_1$, $R_2$ and $R_3$ is 1.5 to 3, and the total number of carbon atoms varies from 8 to 40. The acid value of the esters is less than about 35.

The citric ester compositions of this invention are useful as reactive diluents for high solids thermosetting coating composition and as pigment dispersants for use in thermosetting coatings.

DESCRIPTION OF INVENTION

Citric acid ($\beta$-hydroxytricarballylic acid; 2-hydroxy-1,2,3-propanetricarboxylic acid) is a strong organic acid which, in the anhydrous form, melts at 153° C. Nearly all of commercial grade citric acid is produced by fermentation processes. A small amount is recovered from pineapple canning wastes and orange and lemon waste products.

The citric ester compositions of this invention are made by esterifying the acid groups of the acid with hydroxyl functional compounds leaving the tertiary hydroxyl group unreacted.

One class of hydroxyl functional compounds useful in this invention are glycols which contain from 2 to 12 carbon atoms and have at least 1 primary hydroxyl group, e.g., ethylene glycol, 1,2-propylene glycol, 1,3-butylene glycol, 1,4-butylene glycol, 1,6-hexanediol, 1,2-dodecanediol, and the like.

Another class of hydroxyl functional compounds are vicinal epoxides which contain only one epoxide group per molecule and no other groups which are reactive with the carboxylic acid groups of the citric acid under the reaction conditions used herein. The vicinal monoepoxides contain about 2 to about 32 carbon atoms per molecule. The preferred monepoxides are free of other ether groups. These vicinal epoxides are derived from linear, branched, and cyclo olefins, alkyl esters of unsaturated acids, glycidyl esters of monocarboxylic acids, copolymers of isobutylene and butene, and the like.

Particularly useful mono vicinal epoxides are those derived from alpha olefins which contain from 2 to about 18 carbon atoms. Examples of these alpha olefin epoxides are ethylene oxide, 1,2-propylene oxide, 1,2- butylene oxide, 1,2-octylene oxide, 1,2-decylene oxide, 1,2-dodecylene oxide and the like.

Additional useful mono vicinal epoxides are those derived from non-alpha olefins, branched chain olefins and cycloolefins Examples of these compounds are 2,3-butylene oxide, 3,4-hexylene oxide, epoxidized cyclohexene, limonene oxide, and the like.

Other useful mono vicinal epoxides are epoxidized esters of unsaturated acids wherein the acids contain about 18 to about 22 carbon atoms and the ester group is an alkyl group containing 1 to about 8 carbon atoms. Examples of epoxidized esters are methyl epoxy soyate, ethyl epoxy soyate, propyl epoxy linseedate, hexyl epoxy linseedate, and the like.

Epoxidized esters which can be used in this invention are glycidyl esters, particularly, the glycidyl ester of Versatic Acid. Versatic Acid is the trade name for synthetic tertiary monocarboxylic acids having chain lengths of 9 to 19 carbon atoms. Other monoepoxide esters are those derived from dicyclopentadiene diepoxide wherein one epoxide group has been esterified with a monocarboxylic acid.

One more type of useful monoepoxide is the monoepoxide of the copolymer of isobutylene and butene which has an average molecular weight of about 300 to about 400.

Still another class of hydroxyl functional compounds useful in this invention are monohydric primary and secondary alcohols which contain from 1 to 18 carbon atoms, examples of which are methanol, isopropanol, n-butanol, 2-ethylhexanol, decanol, and the like. Additional useful alcohols are the cycloalkanols which contain 5 to 10 carbon atoms, such as cyclopentanol, cyclohexanol, methyl cyclohexanol and the like.

In preparing the compositions of this invention wherein the ester constituents contain three hydroxyl groups, the citric acid can be esterified to completion using a stoichiometric excess of glycol and removing the excess glycol by distillation when the esterification is complete. However, a preferred process for conducting the esterification is to partially esterify the acid groups with the glycol and then to complete the esterification with a mono vicinal epoxide. The partial esterification can be conducted to an acid value of about 75 to about 150 with the glycol followed by reaction with the monoepoxide to the desired acid value, i.e., below about 35.

The esterification can also be conducted entirely with the monoepoxide. However, when all epoxide is used rather than glycol, the epoxide has a tendency to chain extend, i.e., react with itself, thus forming alkylene ether groups. Ether groups in the ester reduce the ultraviolet light resistance of coatings in which the ester has been incorporated.

The use of all glycol in the process produces some diester — both hydroxyl groups of the glycol react — which results in a higher viscosity product. When partial esterification with glycol followed by complete esterification with monoepoxide is used, low viscosity compositions with a minimum of ether formation are produced.

When the compositions of this invention contain less than three hydroxy groups in the ester constituents, i.e., when the composition is a mixed ester, the esterification can be conducted stepwise wherein each constituent is reacted separately. However, it is preferred to conduct the esterification reaction in two stages. In the first stage, the esterification is conducted with the glycol or monohydric alcohol, or mixture of the two. In the second stage, the esterification is conducted with the monoepoxide to an acid value below 35 and, preferably, below 10.

The esterification reaction can be conducted in a water immiscible solvent wherein azeotropic distillation can be used to remove the water of esterification. The reaction can also be conducted using no solvent. Useful solvents are hydrocarbon solvents having a boiling point of about 75° C. to about 140° C., examples of which are benzene, toluene, and xylene. A particularly preferred solvent is cyclohexane.

The esterification reaction between the acid and hydroxyl groups can be catalyzed by well known esterification catalysts, such as para-toluene sulfonic acid, methane sulfonic acid, sulfuric acid, titanate esters, titanium chelates, metal alcoholates and carboxylates, and the like. A particularly preferred catalyst is triphenylphosphite. These esterification catalysts are used in the amount of about 0.1 to about 5 weight percent, preferably about 0.5 to about 2 weight percent, said weight percents being based on the weight of the reactants.

The esterification reaction between the acid and epoxide groups can be catalyzed by the well known carboxylic acid-epoxy catalysts, such as potassium hydroxide, sodium ethoxide, tertiary amines, quaternary ammonium bases and salts, quaternary phosphonium bases and salts, and metal chelates, such as magnesium acetylacetonate, aluminum acetylacetonate, and zirconium acetylacetonate. A preferred catalyst is made from equal parts of a quaternary salt, e.g., benzyltriphenylphosphonium chloride, and a metal chelate, e.g., aluminum acetylacetonate. These catalysts are used in the amounts of about 0.05 to about 1 weight percent, preferably about 0.1 to about 0.5 weight percent, said weight percents being based on the weights of the reactants.

As stated hereinabove, the ester compositions of this invention contain about 1.5 to about 3 hydroxyl groups in addition to the tertiary hydroxyl group on the citric acid moiety. The total number of carbon atoms in the ester constituents vary from about 8 to about 40. If less than 8 carbon atoms are present, the ester is too hydrophilic and/or too volatile. If more than 40 carbon atoms are present, the ester is somewhat hard to handle and is a poor diluent. Preferred ester compositions have the following components in the listed ranges:

butyl — about 0.5 to about 1.5 equivalents
cyclohexyl — 0 to about 1 equivalent
2-hydroxypropyl — about 0 to about 1.5 equivalents
hydroxyethyl — 0 to about 0.5 equivalent
hydroxy $C_8$–$C_{14}$ alkyl — about 0.1 to about 1 equivalent
The total number of equivalents of the components is about 3.

A particularly preferred composition contains about 1.5 equivalents of butyl, about 1 equivalent of hydroxypropyl, and about 0.5 equivalent of hydroxyalkyl containing 10 carbon atoms.

Another preferred composition contains about 0.5 equivalent of butyl, about 1 equivalent of cyclohexyl, about 0.75 equivalent of hydroxypropyl, and about 0.75 equivalent of hydroxyalkyl containing about 8 carbon atoms.

The citric esters of this invention are useful as plasticizers and diluents. They are particularly useful as reactive diluents for thermosetting coating compositions which are cured through reaction with hydroxyl groups, e.g., aminoplast curing of hydroxy containing polyesters and acrylic resins. By using the citric esters in the formulations, viscosities are lowered so that nonvolatiles can be raised, thereby reducing the amount of solvents which are released to the atmosphere or combustion stacks.

The citric esters of this invention are particularly useful as grinding aids for pigments. Grinding times required to obtain Hegman Grind values of 8 can be reduced considerably by using the citric ester as the grinding vehicle, or by using the citric ester in admixture with an aminoplast resin. In the manufacture of paints, particularly industrial paints, e.g., automotive paints, the pigments used in the paints are not added to the paint formulation directly, but are preground in a portion of the vehicle. The resulting pigment paste is then formulated into the paint composition.

In the manufacture of thermosetting acrylic automotive paints which are made from an hydroxy functional acrylic resin and an aminoplast resin, pigment pastes used in the manufacture are generally made by grinding the pigment in a portion of the aminoplast resin. In order to obtain a proper grind (Hegman Grind value of 8) with a pigment such as carbon black, grind times of 24 hours or more are required when the grind is conducted in an aminoplast resin. Use of the citric esters of this invention either as the sole pigment grind vehicle or in admixture with the aminoplast resin reduces the grind times to 14 hours or less.

The aminoplast resins useful in combination with the citric esters of this invention are derived from such amino compounds as urea, N,N'-ethylene urea, dicyandiamide and aminotriazines reacted with an aldehyde and an alcohol. Examples of triazines are melamine, acetoguanamine, benzoguanamine and the like. The preferred amino compound is melamine. Various aldehydes can be used such as acetaldehyde, acrolein, propionaldehyde and the like. The preferred aldehyde is formaldehyde which includes trioxane and paraformaldehyde.

Suitable alcohols are the 1 to 8 carbon monoalcohols, such as methanol, ethanol, isopropanol, n-butanol, isobutanol, hexanol and 2-ethylhexanol. The preferred alcohols are methanol and n-butanol.

The aminoplast resins can be monomeric or polymeric, the monomeric or polymeric nature being dependent on the reaction ratio of the amino compound and the aldehyde as is well known to those skilled in the art. Commercially available aminoplast resins are sold, for example, under the trademarks Cymel and Syn-U-Tex by American Cyanamid Company and Hi-Tek Polymers, Inc. respectively.

Aminoplasts or amino resins are described in detail in "Encyclopedia of Polymer Science and Technology." Volume 2, pages 1-94, which is hereby incorporated by reference.

The pigment grinding is conducted in mills, such as steel ball mills, pebble mills, 2 and 3 roll mills and sand grinders. High speed dispersers can also be used. The preferred grinding apparatuses are ball and pebble mills.

Any of the well known pigments which are used in paint manufacture can be ground into pigment pastes using the citric esters of this invention as the grinding vehicle. Examples of such pigments are carbon black, titanium dioxide, red iron oxide, aluminum metal, lithophone, cadmium reds, cuprous oxide, umbers, ochers, phthalocyanines, quinacridones, hansa yellows, benzidine yellows, and the like. Other examples of useful pigments are disclosed in Kirk-Othmer "Encyclopedia of Chemical Technology", Second Edition, Vol. 15, pages 495-605, which is hereby incorporated by reference. The esters of this invention are particularly useful as grinding vehicles for hard to grind pigments, e.g., carbon black.

As stated hereinbefore, the citric esters of this invention are useful as grinding vehicles for pigments. These esters can be used as the sole vehicle or, in a preferred mode, can be used as a blend with amino resins. Useful blends can contain from 0 to about 99 weight percent amino resin. Preferred blends contain the citric ester of this invention and the aminoresin in the weight ratio of about 65:35 to about 35:65.

In preparing pigment grinds, the amount of pigment used with the vehicle can vary from about 0.1 to about 0.7 parts by weight to 1 part by weight of the vehicle. The preferred amount of pigment is about 0.5 to about 0.7 to 1 part of vehicle.

This invention is described in more detail by the following examples. Parts and percentages unless otherwise designated are parts and percentages by weight.

EXAMPLE 1

To a suitable reactor equipped with an azeotrope trap to collect water were added 1861.9 parts of citric acid, 1076 parts of n-butanol, 736.7 parts of propylene glycol, 300.7 parts of cyclohexane and 25 parts of triphenylphosphite. Heat was applied raising the temperature to 85° C. where refluxing began and distilled water began to separate in the trap. Heating was continued for about 8 hours with the temperature holding at about 85° C. A total of 235 parts of water were collected during this heating period. An additional 10.7 parts of triphenylphosphite and 150.6 parts of cyclohexane were added. Heating was continued for about 14 hours with the temperature rising from 85° C. to 93° C. About 380 parts of water were recovered in the trap. Additional cyclohexane, 69.6 parts, was added and heating at 91° C. was continued for 5 hours and 45 minutes. A total of about 400 parts of water were recovered in the trap. An additional 10.7 parts of triphenylphosphite were added and heating was continued for 4 hours and 20 minutes with the temperature rising to 98° C. A total of about 425 parts of water were recovered in the trap. The reactor was then arranged for vacuum distillation. Vacuum was applied to a pressure of 1.4 cm Hg and heat was applied raising the temperature to 90° C. After heating for about 1 hour, the acid value of the reaction product was 132.6. The reactor was reset for azeotropic distillation. Cyclohexane, 200 parts, and triphenylphosphite, 5 parts, were added and heat was applied raising the temperature to the reflux temperature which was 110° C. Cyclohexane, 100 parts, was added to lower the temperature to 100° C. After 8 hours heating at 100° C., 20.2 parts of water were distilled over. The reactor was arranged for vacuum distillation. Vacuum to 1.8 cm Hg pressure was applied, and heat was applied to a temperature of 118° C. to remove solvent. The partial ester of citric acid had an acid value of 99.7, a viscosity of $Z_2$-$Z_3$, Gardner-Holdt at 25° C., a Gardner color of less than 1, and a % N.V. of 96.4.

To another reactor were added 1125.4 parts of the partial ester prepared above, 351.6 parts of 1,2-epoxy decane, 0.74 part of aluminum acetylacetonate and 0.74 part of benzyltriphenylphosphonium chloride. Heat was applied raising the temperature to 95° C. in 35 minutes. The temperature was held between 90° and 100° C. for 8 hours. The reaction product had an acid value of 31.4 and an epoxide equivalent weight of about 37,000. A portion of this reaction product, 825 parts, was placed in another reactor with an additional 69.6 parts of 1,2-epoxy decane. Heat was applied raising the temperature to 90° C. The temperature was held at about 90° C. for about 20 hours at which time the acid value was 10.7 and the epoxide equivalent weight was 13,000. The reactor was then equipped for vacuum distillation which was continued for one hour and 30 minutes to a pot temperature of 130° C. and a pressure of 6.0 cm of Hg. The resulting product had a viscosity of V-W (Gardner-Holdt at 25° C.), a Gardner color of less than 1, an acid value of 9.7, an epoxide equivalent weight of 21,000 and a nonvolatile content of 97.3%.

EXAMPLE 2

Using the same procedure described in Example 1, 1728.9 parts of citric acid, 999 parts of n-butanol, 556.8 parts of ethylene glycol, 24.6 parts of triphenylphosphite and 160 parts of cyclohexane were heated to 89° C. and were held at 89°-90° C. for 5 hours and 40 minutes while azeotroping water and cyclohexane with removal of the water and return of cyclohexane to the reactor. Additional cyclohexane, 105 parts, was added to control temperature at about 90° C. Heating at about 90° C. was continued for about 7 hours while azeotroping solvent and water. Additional catalyst, 8.2 parts triphenylphosphite, and 140 parts cyclohexane were added. Heating at about 90° C. was continued for about 8 hours. After adding 3.5 parts triphenylphosphite, heating was continued for 4 hours and 40 minutes. About 407 parts water were removed during the heating periods. The solvents were removed by distilling to a pot temperature of 115° C. and holding at this temperature for one hour. The resulting partial citric ester had an acid value of 100.8, a nonvolatile content of 98.2%, a Gardner color of less than 1 and a Gardner-Holdt viscosity at 25° C. of $Z_4$-$Z_5$.

The partial ester, 841.5 parts, was reacted with 307.5 parts of 1,2-epoxy dodecane using 0.57 part of aluminum acetylacetonate and 0.57 part of benzyltriphenylphosphonium chloride as catalysts by slowly adding the epoxy compound to the ester and catalysts over a 4 hour period with the temperature at 60° C. After the addition, the temperature was raised to 80° C. and was held at 80°-85° C. for about 8 hours. The citric ester product had an acid value of 32.2, a viscosity of Y-Z, (Gardner-Holdt at 25° C.), a Gardner color of less than 1, an epoxide equivalent weight of 26,000 and nonvolatile content of 97%.

EXAMPLE 3

To a suitable reactor, citric acid, 962.6 parts, and 1,2-propylene glycol, 380.8 parts, were slowly added with stirring and heating. After 2 hours with the temperature rising from 25° C. to 124° C., all of the citric acid had dissolved. n-Butanol, 556.4 parts, was added over 30 minutes while the temperature dropped to 110° C. Triphenylphosphite, 19 parts, was then added and heat was applied to raise the temperature to 117° C. where refluxing occurred with removal of water in a Barrett trap. After 3 hours at 117° C., the temperature was slowly raised to 140° C. over a 3 hours and 30 minutes period. At this point, the acid value was 101.2 and 181.9 parts of water had been recovered. Vacuum distillation was then begun and continued over a 3 hour period with the pot temperature rising to 150° C. and the vacuum at 13 cm Hg pressure. The resulting partial citric ester had an acid value of 82, a Gardner-Holdt viscosity at 25° C. of $Z_6$-$Z_7$ and a solids content of 98.16%.

To another reactor were added 611.2 parts of the partial citric ester, 0.2 part of aluminum acetylacetonate and 0.2 part of benzyltriphenylphosphonium chloride. Heat was applied raising the temperature to 110° C. 1,2-Epoxydecane, 200.4 parts, was slowly added while keeping the temperature at 101°-108° C. After 3 hours and 15 minutes, about half the epoxy compound had been added. Additional catalyst, 0.2 part aluminum acetylacetonate and 0.2 part benzyltriphenylphosphonium chloride, was added. Addition of the epoxy compound was continued and was completed after 2 hours and 25 minutes. Heating at 100°-110° C. was continued for 11 hours. The temperature was then raised to 136° C. and was held at 130°-136° C. for 40 minutes. The resulting product had an acid value of 11.7, a Gardner-Holdt viscosity at 25° C. of $Z_2$-$Z_3$, an epoxide equivalent weight of 16,600 and a solids content of 97.3%.

EXAMPLE 4

A number of pigment grinds were made using carbon black obtained from Cabot Corporation (Black Pearl 1300) as the pigment, a butylated formaldehyde melamine resin and a citric ester. The grinds were conducted using a steelball mill, a pigment to vehicle weight ratio of 0.6 to 1 and a nonvolatile content of 40% in a solvent blend of 50 parts n-butanol and 50 parts n-butyl acetate. The butylated formaldehyde melamine resin had a Gardner-Holdt viscosity of U-V at 65% non-volatiles at 25° C. Citric ester 4A was the citric ester of Example 1. Citric ester 4B was the citric ester of Example 2. Citric ester 4C was a citric ester of butanol, propylene glycol-1,2 and 1,2-epoxyhexadecane made by the process described in Example 1, wherein the ester components to 1 mole of citric acid were 1.5 moles of n-butanol, 1 mole of propylene glycol-1,2 and 0.6 mole of 1,2-epoxyhexadecane.

Grinds were conducted using the melamine resin as the sole vehicle (V1); using a blend of 48.5 parts melamine resin and 51.5 parts of citric ester 4A (V2); using a blend of 65 parts of melamine resin and 35 parts of citric ester 4B (V3); and citric ester 4C as the sole vehicle (V4).

The completeness of the grind was determined by the Hegman Grind test (ASTM - D1210 - 79) wherein "8" is the ultimate fineness.

The results of the grind test are as follows:

| Vehicle | Time, hrs. | | | | | |
|---|---|---|---|---|---|---|
| | 4 | 6 | 7 | 12 | 14 | 24 |
| V1 | | 4½ | | 6½ | | 8 |
| V2 | 6½ | 7½ | 8 | | | |
| V3 | | 6 | | 7¾ | 8 | |
| V4 | 2 | 4½ | | 7¼ | 8 | |

EXAMPLE 5

A thermosetting acrylic paint was made by blending pigment paste V2, from Example 4, with an acrylic resin and the butylated formaldehyde melamine resin described in Example 4. The thermosetting acrylic resin was a copolymer of methyl methacrylate (15%), butyl methacrylate (40%), butyl acrylate (21.1%), hydroxypropyl methacrylate (22%) and methacrylic acid (1.9%). The paint had the following non-volatile and volatile content.

|  | % of Total Paint |
|---|---|
| Non-Volatile Content |  |
| Grind vehicle (V2) | 4.03 |
| Carbon black | 2.42 |
| Melamine resin | 9.82 |
| Acrylic resin | 34.28 |
| p-Toluene Sulfonic Acid | 0.25 |
|  | 50.80 |
| Volatile Content |  |
| n-Butanol | 14.90 |
| n-Butyl Acetale | 14.90 |
| Methyl Propyl Ketone | 18.46 |
| Isobutanol | 0.2 |
| Isopropanol | 0.74 |
|  | 49.20 |

The paint had a viscosity, as measured by #4 Ford cup, of 37 seconds. When reduced to 46.9% non-volatile, the viscosity was 24 seconds. Another paint was formulated using the same components as described above except pigment paste V1 from Example 4 was used. The grind vehicle was the butylated formaldehyde melamine resin with no citric ester. This paint at 50.8% non-volatiles had a #4 Ford cup viscosity of 50 seconds. When reduced to 45.4% non-volatiles, the viscosity was 25 seconds.

Each of the paints described above were drawn down on steel panels and were cured by heating at 260° F. for 15 minutes, and 300° F. for 15 minutes. The gloss at 60° and 20° was determined according to ASTM D523-80. The gloss values were as follows:

|  | 0.7 mil Thick | | 1.5 mil Thick | | | |
|---|---|---|---|---|---|---|
|  | 260° F. | | 275° F. | | 300° F. | |
|  | 60° | 20° | 60° | 20° | 60° | 20° |
| INVENTION | 87 | 78 | 88 | 70 | 86 | 72 |
| STANDARD | 86 | 75 | 86 | 66 | 86 | 70 |

After aging for 1, 4, 11 and 14 days respectively, coatings were drawn down on steel panels at 1.5 mil thickness and were baked at 275° F. for 15 minutes. The gloss of the paints was then determined.

|  | 1 Day | | 4 Days | | 11 Days | | 14 Days | |
|---|---|---|---|---|---|---|---|---|
|  | 60° | 20° | 60° | 20° | 60° | 20° | 60° | 60° |
| INVENTION | 88 | 75 | 87 | 78 | 87 | 70 | 88 | 70 |
| STANDARD | 87 | 68 | 86 | 75 | 87 | 70 | 86 | 68 |

The adhesion, hardness and impact resistance of the paints were comparable, having a rating of excellent, good, and good respectively for each property.

The principles, preferred embodiments and modes of operation of the present invention have been described in the foregoing specification. The invention which is intended to be protected herein, however is not to be construed as limited to the particular forms disclosed, since they are to be regarded as illustrative rather than restrictive. Variations and changes may be made by those skilled in the art without departing from the spirit and scope of the invention.

What is claimed:

1. A pigment grind comprising pigment and as the grinding vehicle a citric ester wherein the pigment and the grinding vehicle are in the weight ratio of about 0.1 to about 0.7 part of pigment to 1 part of vehicle wherein the citric ester has the formula:

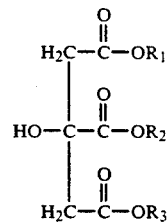

wherein $R_1$ and $R_2$ are selected from:

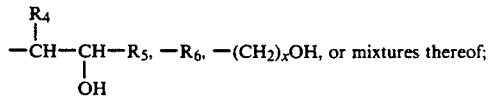

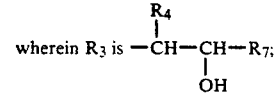

wherein $R_4$ and $R_5$ are H, or an alkyl, cycloalkyl, or alkyl ester group containing 1 to about 32 carbon atoms, wherein said alkyl ester group is derived from epoxidized esters of unsaturated acids or glycidyl esters of monocarboxylic acids, wherein the total number of carbon atoms in $R_4$ and $R_5$ is 0 to about 32;

wherein $R_6$ is an alkyl group containing 1 to about 18 carbon atoms, or a cyclo alkyl group containing 5 to about 10 carbon atoms; wherein $R_7$ is an alkyl, cycloalkyl, or alkyl ester group containing 4 to about 32 carbon atoms, wherein said alkyl ester group is derived from epoxidized esters of unsaturated acids or glycidyl esters of monocarboxylic acids, and wherein x has a value of 3 to 6;

wherein $R_1$, $R_2$ and $R_3$ are so selected that the total number of OH groups in $R_1$, $R_2$ and $R_3$ is about 1.5 to 3 and the total number of carbon atoms in $R_1$, $R_2$ and $R_3$ is 8 to about 40; and wherein the acid value of the ester is less than about 35.

2. The pigment grind of claim 1 wherein the grind contains about 0.5 to about 0.7 part of pigment to 1 part of vehicle.

3. The pigment grind of claim 1 wherein the vehicle contains up to 99 weight percent aminoresin based on the weight of aminoresin and citric ester.

4. The pigment grind of claim 3 wherein the vehicle contains from about 65 to about 35 parts by weight of citric ester and about 35 to about 65 parts by weight of aminoresin, the total parts being 100.

5. The pigment grind of claim 3 wherein the aminoresin is a butylated formaldehyde melamine resin.

6. The pigment grind of claim 1 wherein $R_1$, $R_2$ and $R_3$ are derived from glycols which contain from 2 to 12 carbon atoms and at least one primary hydroxyl group, a vicinal epoxide compound which contains only one epoxide group per molecule, or a primary or secondary alcohol which contains from 1 to 18 carbon atoms.

7. The pigment grind of claim 6 wherein the vicinal epoxide compound is an alpha olefin which contains from 2 to about 18 carbon atoms.

8. The pigment grind of claim 6 wherein the vicinal epoxide compound is an epoxidized ester of an unsaturated acid wherein the acid contains about 18 to about 22 carbon atoms and the ester group is an alkyl group containing about 1 to about 8 carbon atoms.

9. The pigment of claim 6 wherein the vicinal epoxide compound is a glycidyl ester of Versatic Acid.

10. The pigment grind of claim 6 wherein the vicinal epoxide compound is a monoepoxide of a copolymer of isobutylene and butene having an average molecular weight of about 300 to about 400.

11. The pigment grind of claim 1 wherein the R substituents of the citric ester are the following organic radicals in the following equivalent amounts:

butyl — about 0.5 to about 1.5
cyclohexyl — 0 to about 1
hydroxypropyl — about 0 to about 1.5
hydroxyethyl — 0 to about 0.5
hydroxy $C_8$–$C_{14}$ alkyl — about 0.1 to about 1
wherein the total number of equivalents is 3.

12. The pigment grind of claim 1 wherein the ester contains about 1.5 equivalents of butyl, about 1 equivalent of hydroxypropyl, and about 0.5 equivalent of hydroxyalkyl wherein the alkyl group contains 10 carbon atoms.

13. The pigment grind of claim 1 wherein the ester contains about 0.5 equivalent of butyl, about 1 equivalent of cyclohexyl, about 0.75 equivalent of hydroxypropyl, and about 0.75 equivalent of hydroxyalkyl containing 8 carbon atoms.

* * * * *